United States Patent
Rao et al.

(10) Patent No.: US 10,315,134 B2
(45) Date of Patent: Jun. 11, 2019

(54) CHROMATOGRAPHY COLUMN ASSEMBLY WITH SNAP FIT END CAP AND ADAPTOR SHAFT

(71) Applicant: GE Healthcare Bio-Sciences AB, Uppsala (SE)

(72) Inventors: Veena Rao, Bangalore (IN); Manoj Ramakrishna, Bangalore (IN); Nikhil Kamble, Bangalore (IN)

(73) Assignee: GE Healthcare Bio-Science AB, Uppsala (SE)

(*) Notice: Subject to any disclaimer, the term of this patent is extended or adjusted under 35 U.S.C. 154(b) by 346 days.

(21) Appl. No.: 15/022,813

(22) PCT Filed: Aug. 15, 2014

(86) PCT No.: PCT/EP2014/067492
§ 371 (c)(1),
(2) Date: Mar. 17, 2016

(87) PCT Pub. No.: WO2015/043830
PCT Pub. Date: Apr. 2, 2015

(65) Prior Publication Data
US 2016/0228792 A1    Aug. 11, 2016

(30) Foreign Application Priority Data
Sep. 27, 2013  (IN) .......................... 2866/DEL/2013

(51) Int. Cl.
*G01N 30/60* (2006.01)
*B01D 15/22* (2006.01)
(Continued)

(52) U.S. Cl.
CPC .......... *B01D 15/424* (2013.01); *B01D 15/22* (2013.01); *C07K 1/16* (2013.01); *G01N 30/6004* (2013.01); *G01N 30/6021* (2013.01)

(58) Field of Classification Search
None
See application file for complete search history.

(56) References Cited

U.S. PATENT DOCUMENTS

| | | | |
|---|---|---|---|
| 4,133,562 A | 1/1979 | Andrén | |
| 4,451,364 A * | 5/1984 | Higgins | G01N 30/6026 210/198.2 |

(Continued)

FOREIGN PATENT DOCUMENTS

| | | |
|---|---|---|
| CN | 201676560 U | 12/2010 |
| CN | 102713600 A | 10/2012 |

(Continued)

OTHER PUBLICATIONS

Machine translation of DE4006351 (A1) to Edgar Grom. (Year: 1991).*

(Continued)

*Primary Examiner* — Christopher Adam Hixson
*Assistant Examiner* — Michelle Adams
(74) *Attorney, Agent, or Firm* — Wood IP LLC

(57) ABSTRACT

The invention relates to a chromatography column assembly that offers an affordable self-packed column for performing chromatographic separation. The chromatography column assembly comprises a column tube having a first and a second opening at substantially opposite ends, and an end cap of either a snap fit design or a bolted design. The column assembly may further include an adaptor shaft inserted into the column through the end cap for achieving a desired bed volume. The column assembly may also include a second end cap enclosing the second opening, and an optional adaptor shaft may be inserted into the column through the second end cap, enabling further adjustment of the bed volume.

18 Claims, 3 Drawing Sheets

(51) Int. Cl.
*B01D 15/42* (2006.01)
*C07K 1/16* (2006.01)

(56) References Cited

U.S. PATENT DOCUMENTS

| | | |
|---|---|---|
| 4,737,292 A | 4/1988 | Ritacco et al. |
| 5,378,361 A | 1/1995 | Baeckström |
| 2005/0242018 A1 | 11/2005 | Hodgin et al. |
| 2006/0180536 A1 | 8/2006 | Cummings |

FOREIGN PATENT DOCUMENTS

| | | |
|---|---|---|
| CN | 102895801 A | 1/2013 |
| CN | 103083943 A | 5/2013 |
| DE | 4006351 A1 | 9/1991 |
| EP | 3049804 A1 | 8/2016 |
| WO | 02053256 A1 | 7/2002 |
| WO | 2011124709 A1 | 10/2011 |
| WO | 2015/043830 A1 | 4/2015 |

OTHER PUBLICATIONS

International Search Report and Written Opinion for PCT/EP2014/067492, dated Nov. 7, 2014, 11 pages.
International Preliminary Report on Patentability received for PCT Patent Application No. PCT/EP2014/067492, dated Mar. 29, 2016, 7 pages.
Office Action Received for Chinese Patent Application No. 201480053202.0, dated Jan. 25, 2017, 23 pages, (Official Copy 11 pages+English Translation 12 Pages).

* cited by examiner

US 10,315,134 B2

CHROMATOGRAPHY COLUMN ASSEMBLY WITH SNAP FIT END CAP AND ADAPTOR SHAFT

This application is a filing under 35 U.S.C. 371 of international application number PCT/EP2014/067492, filed Aug. 15, 2014, which claims priority to Indian application number 2866/DEL/2013, filed Sep. 27, 2013, the entire disclosures of each of which are hereby incorporated by reference.

FIELD OF THE INVENTION

The present invention relates to the purification of cellular components such as proteins and/or peptides using liquid chromatography. More specifically, the invention relates to a chromatography column and a kit for the purification of one or more cellular components, as well as a method of use thereof.

BACKGROUND OF THE INVENTION

Biotechnological methods are used to an increasing extent in the investigation of proteins, peptides, nucleic acids and other biological entities. Due to its versatility and sensitivity to the entities, chromatography is often the preferred purification method in this context. The chromatography is based on principle of separating mixture by dissolving a mixture in a mobile phase (e.g. liquids like buffers) and passing it through a stationary phase (e.g., chromatography matrix that could be beads/resins). More specifically, a mixture which includes the target entity (e.g., a chemical/biological molecule) is introduced into a mobile phase, the mobile phase is then contacted with a stationary phase, also known as the chromatography matrix. The target entity will then undergo a series of interactions between the stationary and mobile phases as it is being carried through the stationary matrix by the mobile phase. The interactions exploit differences in the physical or chemical properties of the target entity and other components in the mixture.

Chromatographic methods can be run in different modes of operation. The simplest mode is batch chromatography, wherein the mobile phase is added to a vessel containing stationary phase; interaction between target entity and stationary phase is allowed for a suitable period of time; the mobile phase is withdrawn; and an eluent is added to release the target entity. In column chromatography on the other hand, a mobile phase containing the sample (mixture) is added to the top of a column containing stationary phase. By opening up an outlet at the lower end of the column, the mobile phase is passed through the column, during which the sample interacts with the stationary phase. Elution is commonly performed by applying a small amount of eluent at the top, and again allowing the eluent to pass through the column either by gravity or using a chromatography system.

Once a suitable load of target entity has been obtained on the stationary phase, the liquid flow is changed from mobile phase to an eluent, optionally with one or more intermediate washings, and the target fraction is recovered from the eluent at the outlet of the column. The eluent will commonly comprise a gradient, such as a salt or pH gradient. To avoid contamination of large contaminants, and to obtain an advantageous liquid distribution throughout the column, the inlet is usually equipped with a filter and mechanical liquid distributor means. Most commonly, the outlet will similarly present both a filter and some mechanical liquid distributor means.

Many researchers who perform protein purification uses either a basic chromatography system or by manual methods. Due to the workflow compulsion, most of these users resort to self-packed empty columns, packing their own column with the media of their choice. A number of vendors offer empty columns in the field. Bio-Rad provides a low pressure chromatography column under the Econo brand. These are glass columns with flow adaptors, and withstand a low operating pressure of less than 1 bar. Pall Corporation provides LRC columns which can withstand an operating pressure of 10-30 bars. Their screw-lock system allows rapid coarse adjustment followed by precise fine adjustment of the piston (which gives coverage of the various bed heights).

Users who choose to pack their own columns face constant challenges in terms of limited pressure specification in low pressure column segment, affordability, ease of use, complex designs of endcap with adaptors, and limitation in the size/scale of columns. There is a need for better chromatography column design that is more user friendly and can withstand higher column pressure.

BRIEF SUMMARY OF THE INVENTION

Disclosed herein are novel chromatography column designs and method of using such. Thus, a first aspect of the present invention is to provide a self-packed chromatography column assembly incorporating a novel end cap design, which is suitable for the purification of biomolecules such as proteins and/or peptides from a starting biological material.

A specific aspect of the invention provides a novel end cap for the column assembly, which is a snap fit end cap. Such a column may take a backpressure of up to 2 bars.

Another specific aspect of the invention provides a novel end cap for a column assembly, which is an end cap with bolted design using a retainer or circlip. Such a column may take a backpressure of up to 5 bars.

A second aspect of the present invention is to provide a method of chromatographic separation of biomolecules using the self-packed chromatography column assembly including the novel end caps according to certain embodiments of the invention.

A third aspect of the present invention provides a kit for making a chromatography column assembly, which kit contains the novel end cap components according to certain embodiments of the invention.

Further details and advantages of the present invention will appear from the description and claims below.

DETAILED DESCRIPTION OF THE INVENTION

The invention relates to a chromatography column assembly that offers an affordable self-packed column for performing chromatographic separation including but not limited to affinity, ion exchange, gel filtration, desalting and buffer exchange of biomolecules such as proteins using either a chromatographic system or by gravity flow. The modular design of the chromatography column assembly offers certain advantages, e.g., ease of use, self-assembly options and autoclavability.

In a first aspect, the present invention relates to a liquid chromatography column assembly comprising a column tube having a first and a second opening at substantially opposite ends, and an end cap according to certain embodiments of the invention, enclosing the first opening. Optionally, the column assembly further includes an adaptor shaft inserted into the column from the first opening for achieving a desired bed volume. The column assembly may further include a second end cap enclosing the second opening. In certain embodiments, the second end cap is one according to any of the prior art designs. In other embodiments, the second end cap is one according to certain embodiments of the invention, and an optional adaptor shaft is inserted into the column through the second end cap, enabling further adjustment of the bed volume.

In one embodiment, the invention provides an end cap that is of the snap fit design. The use of a snap fit end cap enables the chromatography column assembly to withstand a higher column pressures than certain prior art end caps. This column may take a backpressure of up to 2 bars. The snap fit design also renders the column assembling process easy to complete and thus is very user friendly. While in the presence of the adaptor shaft, this chromatography column assembly may be used with any chromatographic system; irrespective of the presence of the adaptor shaft, the novel chromatography column assembly allows the user to perform gravity flow operations.

In a variation of the embodiment, the invention provides an end cap of a snap fit design with internal thread, as well as a moveable adapter shaft with complementary thread. The inclusion of movable adaptors (combination of one or two or none) allows the user to generate different bed volumes and use the column on either chromatography system or by gravity flow methods.

Figure 1A:
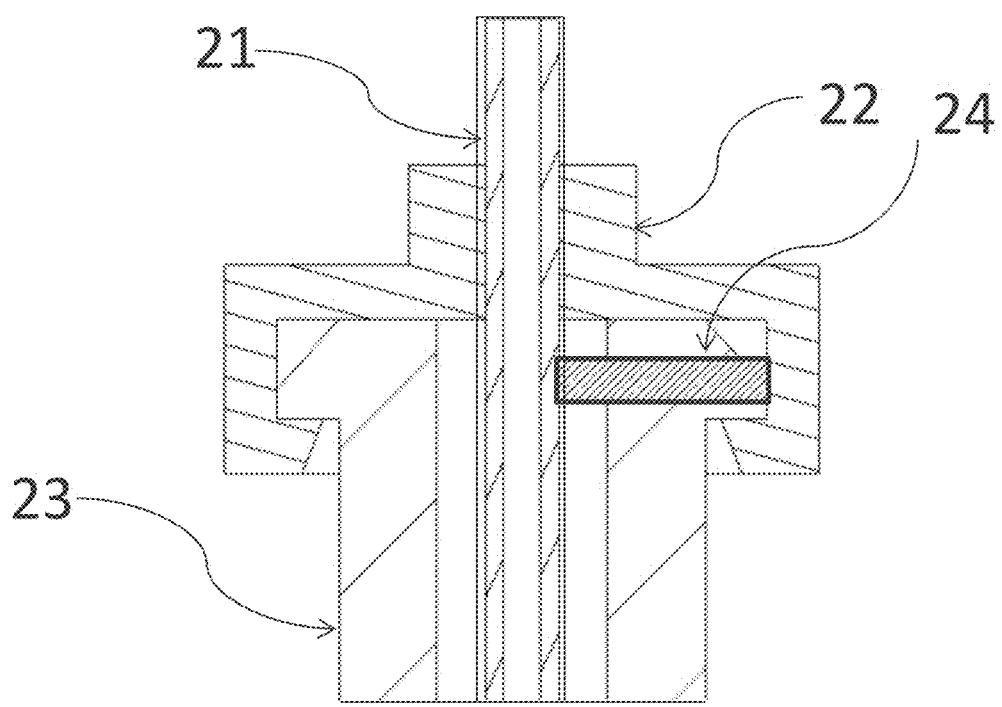
FIG. 1A shows a schematic of part of a chromatography column assembly, showing the end cap, adaptor shaft, pin stopper, as well as part of the column tube, according to one embodiment of the invention.
Figure 1B:
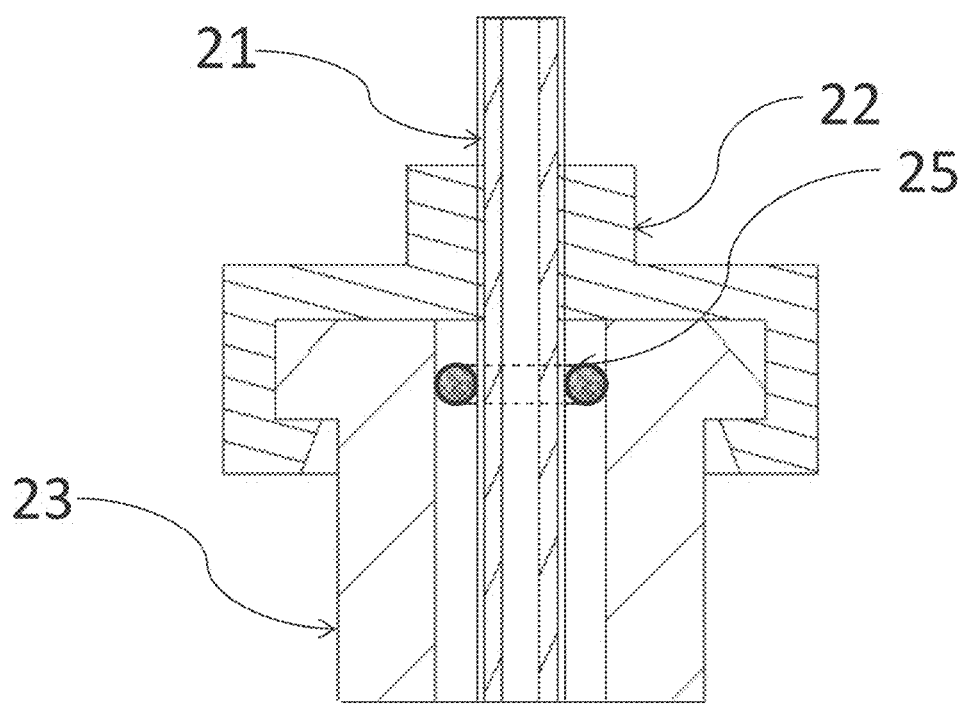
FIG. 1B is a schematic diagram of part of a chromatography column assembly, showing the end cap, adaptor shaft, O-ring, as well as part of the column tube, according to another embodiment of the invention.

In another variation of the embodiment, in addition to the end cap of a snap fit design with internal thread (22) and the moveable adapter shaft with complementary thread (21), a concealed pin (i.e., stopper) (24) is included across a part of the rim of the column tube (23) near the first open end (FIG. 1A). The concealed pin prevents rotation of the adaptor shaft along with the end cap (due to friction) thus enabling easy adjustment of bed height. Alternatively, an O-ring (25, as shown in FIG. 1B) may be used to introduce friction between the adaptor shaft and the column tube to prevent adaptor rotation.

The snap fit design of the end cap makes a column assembly extremely user friendly and may operate at up to 2 bars of back pressure. The design allows the user to achieve various bed heights with combination of one or two adaptors. It also allows the user to use this column for gravity flow application without the use of a chromatography system.

Figure 2:
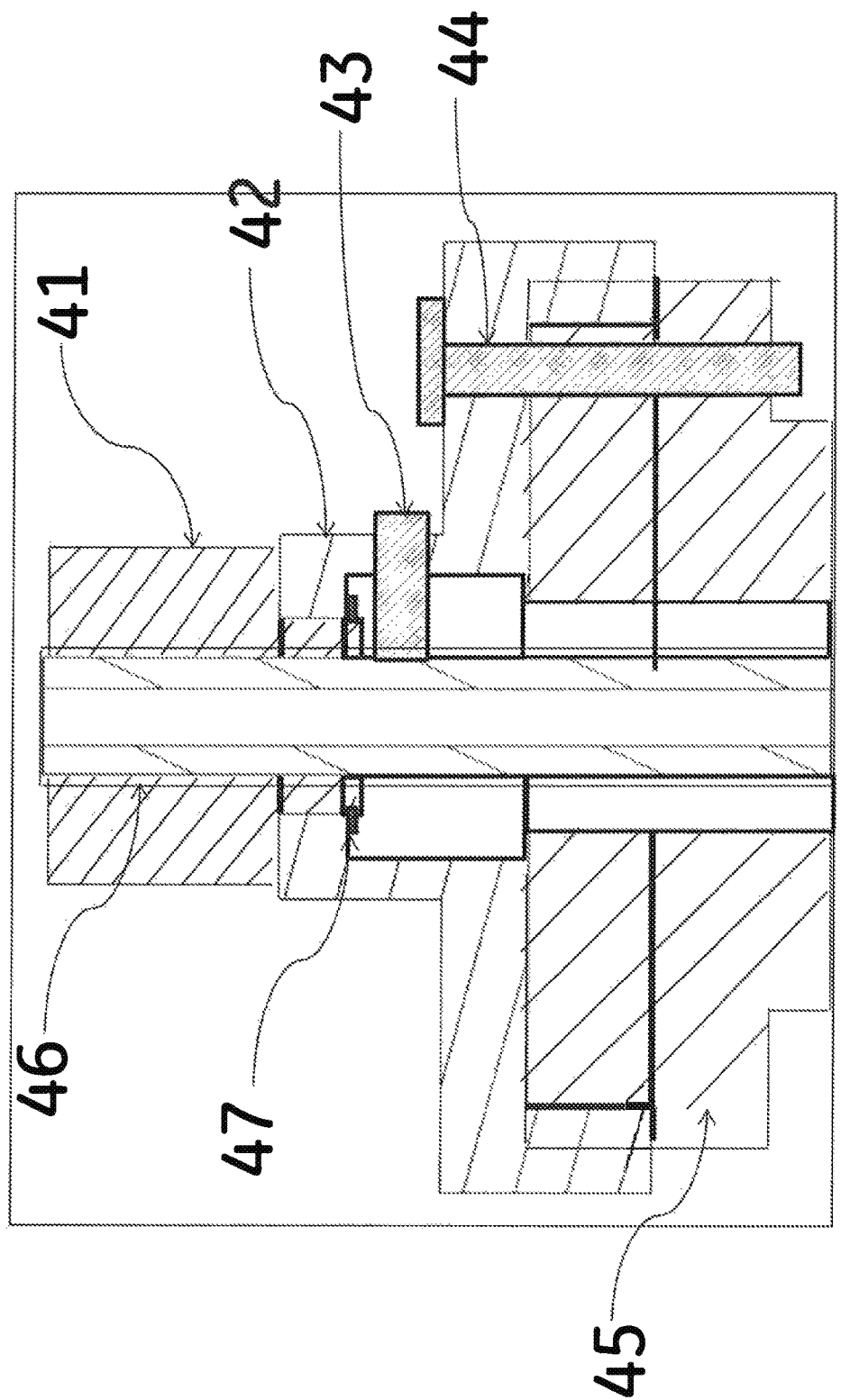
FIG. 2 shows a schematic of part of a chromatography column assembly, showing the bolted design of the end cap, retainer/circlip as well as part of the column tube, according to one embodiment of the invention.

In another embodiment, the invention provides an end cap that is of the bolted design (FIG. 2). The end cap (42) is bolted onto the rim of the column (45) near the first open end with a bolt (44) thus enclosing the first opening. An end cap nut (41) with internal threads is engaged with the adapter shaft (46) that has complementary threads. The use of the movable adaptor shafts (combination of one or two or none) allows the user to adjust bed volumes. An optional pin stopper (43) may be included on the end cap (42). The stopper prevents rotation of the adaptor while the end cap nut is been rotated, thus enabling easy adjustment of bed height. The end cap nut is secured to the bolted end cap by means of a circlip or any type of retainer [47].

The bolted design of the end cap allows the user to use these column assemblies with chromatography systems. These column assemblies may withstand up to 5 bars of back pressure. The design allows the user to achieve various bed heights with combination of one or two adaptors.

The column tube may be made out of any biocompatible material that offers chemical resistance to most of the chemicals used during routine purification of biomolecules. Thus, the chromatography tube may be made e.g. from a suitable plastic material, steel or glass. In certain embodiments, the column tube is made of acrylic or polypropylene material. Preferably, the column tube is transparent. The column tube may further include conventional elements such as filters, distribution means, tubing, fittings, bags, etc.

The column tube may have different length and internal diameters, in so far as the end cap, adaptor and related components are made with matching size. In certain embodiments, the chromatography column assembly provides a column bed volume of from 1-170 mL. Preferably, the chromatography column assembly with a snap fit end cap has a column bed volume of from 1-70 mL. Also preferably, the chromatography column assembly with a bolted end cap has a column bed volume of from 2-130 mL.

In certain embodiments, the internal diameter of the column tube is between 5-50 mm, while the length of the column tube is between 50-1000 mm. In certain preferred embodiments, the column tube for the column assembly with a snap fit end cap has a diameter of 10 mm and a length of 100, 200 or 400 mm respectively. In certain other embodiments, the column tube for the column assembly with a snap fit end cap has a diameter of 16 mm and a length of 200 mm. In certain other preferred embodiments, the column tube for the column assembly with a bolted end cap has a diameter of 60 mm and a length of 200, 400 or 700 mm respectively.

In certain embodiments, the adaptor shaft may be made out of any biocompatable material that offers chemical resistance to most of the chemicals used during routine purification of biomolecules. Thus, the adaptor shaft may be made e.g. from a suitable plastic material. In certain embodiments, the adaptor shaft for the column assembly with a snap fit end cap is made of polypropylene material. In certain embodiments, the adaptor shaft for the column assembly with a bolted end cap is made of a high strength material, in order to withstand the operating pressure. For example, Grivory GVX-5H natural may be a suitable material. Grivory GVX-5H natural is a 50% glass fibre reinforced engineering thermoplastic material based on a combination of semicrystalline polyamide with partially aromatic copolyamide. Grivory GVX-5H natural has an optimized flowability and is suitable for injection moulding technical parts, exhibiting exceptional characteristics even after moisture absorption: high stiffness and strength; high dimensional stability, very low warpage; good chemical resistance; and very good surface finish. Another exemplary material is PEEK 450G especially when high strength is required. Furthermore, the material could be any number of other glass/carbon filled biocompatible plastic as well.

In certain embodiments, the adaptor shaft, at the end that is inserted into the column, may include a distribution plate. The distribution plate allows the homogenous distribution of in-coming liquid in the column thus offering increased column performance.

In certain embodiments, the end cap may be made out of any material that does not erode the adaptor material very quickly.

The liquid chromatography column assembly according to the present invention is easy to use. The modular design allows better and faster assembling of the column assembly. The alternative designs also allow user the ability to operate between 2 to 5 bars pressure using basic chromatography system, and provides the ability for gravity flow applications. The design may be applied to provide chromatography column assembly for any basic liquid chromatography system on the market. It also offers a complete solution by allowing the user to perform different types of purification using Affinity, Ion Exchange, Gel filtration and Desalting techniques using either of these alternatively designed columns. Furthermore, the columns are much more affordable and have superior pressure specification when compared with immediate competitor offerings.

In a second aspect of the present invention, it is provided a method for the separation of biomolecules using the self-packed chromatography column assembly including the novel end cap designs.

In one exemplary embodiment, the present invention relates to the use of the chromatography column assembly according to certain embodiments of the invention for purification of one or more target cellular components from a crude cell lysate by continuous liquid chromatography, which method comprises the steps of (a) lysis of cells in a vessel to provide a crude cell lysate, and optionally clarifying the cell lysate;

(b) passing the cell lysate so obtained over a chromatography column assembly according to certain embodiments of the invention, packed with a suitable chromatography matrix to adsorb the target component(s);

(c) recovering the target component(s) by contacting the matrix with an elution buffer that releases adsorbed component(s).

Chemical and mechanical lysis of cells contained in liquids such as fermentation broths are well known in this field. The chemical lysis can be carried out with any suitable lytic reagent, such as detergent, a lytic enzyme, or a chaotrope. In an advantageous embodiment, the lytic reagent used in step (a) is an enzyme. In a specific embodiment, the chemical lysis is obtained by adding lysozyme in a suitable amount and under the appropriate conditions. Mechanical lysis is also well known in this field, and commonly used methods include sonication, French press cell, homogenization, grinding, and freeze-thaw lysis. As the skilled person in this field will realize, the duration of the mechanical lysis should be adapted to be long enough to avoid clogging of filters in the downstream process, but short enough not to denature the desired target proteins and/or peptides. In one embodiment, step (a) comprises both a chemical and a mechanical lysis. The mechanical lysis is then performed subsequent to the chemical lysis by any well-known method such as sonication. In a preferred embodiment of the present method, step (a) comprises addition of lysozyme followed by sonication. The crude cell lysate so obtained is then optionally clarified before been direct added to a chromatography column.

The choice of a chromatography matrix is well known by a skilled person in the field, for commonly used chromatography separation methods such as affinity, ion exchange, gel filtration, desalting or buffer exchange.

As is well known, the chromatography matrix is commonly equilibrated with a suitable binding buffer before addition of sample. The sample is preferably combined with binding buffer to obtain suitable conditions for adsorption (binding). Thus, in one embodiment, in step (a), the lysate is combined with a binding buffer to provide a mobile phase of suitable pH. An illustrative binding buffer will contain urea and guanidine. The volume applied will depend on the scale of the process. In one embodiment, the present method is carried out in analytical scale, and the mobile phase volume is then up to 50 ml, such as 1-50 ml, for example 1 ml or 5 ml.

Elution is commonly performed according to standard protocols in this field, which commonly involves addition of an elution buffer. Alternatively, elution is performed by lowering the pH. The elution buffer may be added as a continuous or stepwise pH gradient. Such gradient elution would be used at least to determine the optimal elution conditions for a given process, and once such conditions have been determined an elution buffer of the optimal pH may be added in step (c).

The cells from which the crude lysate originates may be any prokaryotic or eukaryotic cell, such as bacteria, yeast etc. The target component can be any cellular component, such as a polypeptide, protein, protein fragment, DNA, RNA, other nucleotide sequence, carbohydrate, lipid, cholesterol, or kinase. In one embodiment, at least one target component is a protein. A target protein may be of a size anywhere in the range of 10000-200000 Da. In one advantageous embodiment of the present method, at least one target component is a peptide.

In another exemplary embodiment, the present invention relates to the use of the chromatography column assembly according to certain embodiments of the invention for separation of a biomolecule of interest from a mixture, which method comprises the steps of (a) packing a chromatography column assembly according to certain embodiments of the invention, with a suitable chromatography matrix;

(b) passing the mixture over the chromatography column to adsorb the biomolecule of interest;

(c) contacting the matrix with an elution buffer that releases the adsorbed biomolecule of interest; and (d) collecting the biomolecule of interest.

In a third aspect of the present invention, it is provides a kit for making a chromatography column assembly. The kit comprises, in separate compartments, an end cap according to the invention and a column tube.

In certain embodiments, the end cap in the kit is a snap fit end cap. In a preferred embodiment, the snap fit end cap includes internal thread, and the kit also includes an adaptor shaft that includes complementary thread. In another embodiment, the column tube contains a pin stopper on its rim near an open end.

In certain embodiments, the kit further comprises a bolt, an end cap nut with internal thread, a retainer ring, an adapter shaft (46) with complementary thread, and both the end cap and the column tube contains an opening for the bolt. In one embodiment, the end cap includes a pin stopper that prevents movement of the end cap while the adaptor shaft is been rotated in relation to the column tube.

In certain embodiments, the kit may also comprise additional equipment useful for chromatographic separation of biomolecules.

In an advantageous embodiment, the kit further comprises instructions, such as written or electronically saved instructions.

While the particular embodiment of the present invention has been shown and described, it will be obvious to those skilled in the art that changes and modifications may be made without departing from the teachings of the invention. The matter set forth in the foregoing description and accompanying drawings is offered by way of illustration only and not as a limitation. The actual scope of the invention is intended to be defined in the following claims when viewed in their proper perspective based on the prior art.

We claim:

1. A liquid chromatography column assembly comprising:
   a chromatography column comprising a column tube having a first opening and a rim at a first end and a second opening at a second end that is opposite to the first end;
   a snap fit end cap that encloses the first opening through engagement with the rim; and
   an adaptor shaft having an end that is inserted through the snap fit end cap and the first opening into the column tube, wherein the snap fit end cap contains internal thread and the adaptor shaft contains complementary thread that is complementary to the internal thread.

2. The liquid chromatography column assembly of claim 1, wherein the assembly may take a backpressure of up to 2 bars.

3. The liquid chromatography column assembly of claim 1, further comprising a concealed pin across a part of the rim of the first end of the column tube into the first opening and in contact with the adaptor shaft to prevent rotation of the adaptor shaft relative to the snap fit end cap.

4. The liquid chromatography column assembly of claim 1, further comprising an O-ring sandwiched between the adaptor shaft and the column tube to introduce friction between the adaptor shaft and the column tube to prevent rotation of the adaptor shaft.

5. The liquid chromatography column assembly of claim 1, further comprising a second adaptor shaft inserted through the second opening into the column tube.

6. The liquid chromatography column assembly of claim 1, further comprising a second snap fit end cap that encloses the second opening.

7. The liquid chromatography column assembly of claim 1, wherein the end of the adaptor shaft that is inserted into the column tube includes a distribution plate to allow homogenous distribution of in-coming liquid in the column tube.

8. A method for the separation of a biomolecule of interest from a mixture, which method comprising
   (a) packing a chromatography column assembly of claim 1 with a suitable chromatography matrix;
   (b) passing the mixture over the chromatography column to adsorb the biomolecule of interest;
   (c) contacting the matrix with an elution buffer that releases the adsorbed biomolecule of interest; and
   (d) collecting the biomolecule of interest.

9. A liquid chromatography column assembly comprising:
   a chromatography column comprising a column tube having a first opening and a first rim at a first end and a second opening and a second rim at a second end that is opposite to the first end;
   a snap fit end cap enclosing the first opening through engagement with the first rim; and
   an adaptor shaft having an end that is inserted through the snap fit end cap and the first opening into the column tube, wherein the snap fit end cap contains internal thread and the adaptor shaft contains complementary thread that is complementary to the internal thread such that the adaptor shaft is engaged with the snap fit end cap through the complementary thread.

10. The liquid chromatography column assembly of claim 9, further comprising an O-ring sandwiched between the adaptor shaft and the column tube to introduce friction between the adaptor shaft and the column tube to prevent rotation of the adaptor shaft.

11. The liquid chromatography column assembly of claim 9, wherein the end of the adaptor shaft that is inserted into the column tube includes a distribution plate to allow homogenous distribution of in-coming liquid in the column tube.

12. The liquid chromatography column assembly of claim 9, further comprising a second adaptor shaft inserted through the second opening into the column tube.

13. The liquid chromatography column assembly of claim 9, further comprising a second snap fit end cap that encloses the second opening through engagement with the second rim.

14. A method for the separation of a biomolecule of interest from a mixture, which method comprising
   (a) packing a chromatography column assembly of claim 9 with a suitable chromatography matrix;
   (b) passing the mixture over the chromatography column to adsorb the biomolecule of interest;
   (c) contacting the matrix with an elution buffer that releases the adsorbed biomolecule of interest; and
   (d) collecting the biomolecule of interest.

15. A liquid chromatography column assembly comprising:
   a column tube having a first opening and a first rim at a first end and a second opening and a second rim at a second end that is opposite to the first end;
   a snap fit end cap enclosing the first opening through engagement with the first rim;
   an adaptor shaft having an end that is inserted through the snap fit end cap and the first opening into the column tube, wherein the snap fit end cap contains internal thread and the adaptor shaft contains complementary thread that is complementary to the internal thread such that the adaptor shaft is engaged with the snap fit end cap through the complementary thread; and
   a concealed pin across a part of the first rim into the first opening and in contact with the adaptor shaft to prevent rotation of the adaptor shaft relative to the snap fit end cap.

16. The liquid chromatography column assembly of claim 15, wherein the end of the adaptor shaft that is inserted into the column tube includes a distribution plate to allow homogenous distribution of in-coming liquid in the column tube.

17. The liquid chromatography column assembly of claim 15, further comprising a second adaptor shaft inserted through the second opening into the column tube.

18. The liquid chromatography column assembly of claim 15, further comprising a second snap fit end cap that encloses the second opening through engagement with the second rim.

* * * * *